US007696178B2

(12) United States Patent
Malvolti et al.

(10) Patent No.: US 7,696,178 B2
(45) **Date of Patent: *Apr. 13, 2010**

(54) OPTIMISED FORMULATION OF TOBRAMYCIN FOR AEROSOLIZATION

(75) Inventors: Chiara Malvolti, Parma (IT); Raffaella Garzia, Parma (IT)

(73) Assignee: Chiesi Farmaceutici S.p.A., Parma (IT)

( * ) Notice: Subject to any disclaimer, the term of this patent is extended or adjusted under 35 U.S.C. 154(b) by 276 days.

This patent is subject to a terminal disclaimer.

(21) Appl. No.: 11/083,139

(22) Filed: Mar. 18, 2005

(65) Prior Publication Data

US 2005/0163722 A1 Jul. 28, 2005

Related U.S. Application Data

(63) Continuation of application No. 10/482,224, filed as application No. PCT/EP02/06544 on Jun. 14, 2002, now Pat. No. 6,987,094.

(30) Foreign Application Priority Data

Jul. 2, 2001 (EP) .................................. 01116071

(51) Int. Cl.
*A61K 31/70* (2006.01)
*A61K 31/7036* (2006.01)

(52) U.S. Cl. ............................ 514/40; 514/36; 514/35; 514/25; 536/4.1; 536/55.3; 536/124

(58) Field of Classification Search .................. 514/40, 514/36, 35, 25; 536/4.1, 55.3, 124; 53/124
See application file for complete search history.

(56) References Cited

U.S. PATENT DOCUMENTS

| | | | |
|---|---|---|---|
| 3,361,306 | A | 1/1968 | Grim |
| 3,622,053 | A | 11/1971 | Ryden |
| 4,185,100 | A | 1/1980 | Rovee et al. |
| 4,499,108 | A | 2/1985 | Sequeira et al. |
| 4,579,854 | A | 4/1986 | Iwakuma et al. |
| 4,584,320 | A | 4/1986 | Rubin et al. |
| 4,835,145 | A | 5/1989 | MacDonald |
| 5,190,029 | A | 3/1993 | Byron et al. |
| 5,192,528 | A | 3/1993 | Radhakrishnan et al. |
| 5,415,853 | A | 5/1995 | Hettche et al. |
| 5,435,297 | A | 7/1995 | Klein |
| 5,508,269 | A | 4/1996 | Smith et al. |
| 5,605,674 | A | 2/1997 | Purewal et al. |
| 5,642,728 | A | 7/1997 | Andersson et al. |
| 5,653,961 | A | 8/1997 | McNally et al. |
| 5,676,930 | A | 10/1997 | Jager |
| 5,683,677 | A | 11/1997 | Purewal et al. |
| 5,695,743 | A | 12/1997 | Purewal et al. |
| 5,776,433 | A | 7/1998 | Tzou et al. |
| 5,891,419 | A | 4/1999 | Cutie |
| 5,954,047 | A | 9/1999 | Armer et al. |
| 5,955,058 | A | 9/1999 | Jager et al. |
| 6,004,537 | A | 12/1999 | Blondino et al. |
| 6,006,745 | A | 12/1999 | Marecki et al. |
| 6,026,808 | A | 2/2000 | Armer et al. |
| 6,045,778 | A | 4/2000 | Jager et al. |
| 6,045,784 | A | 4/2000 | Ruebusch et al. |
| 6,131,566 | A | 10/2000 | Ashurst |
| 6,143,277 | A | 11/2000 | Ashurst et al. |
| 6,149,892 | A | 11/2000 | Britto |
| 6,150,418 | A | 11/2000 | Hochrainer et al. |
| 6,241,969 | B1 | 6/2001 | Saidi et al. |
| 6,253,762 | B1 | 7/2001 | Britto |
| 6,290,930 | B1 | 9/2001 | Blondino et al. |
| 6,315,985 | B1 | 11/2001 | Wu et al. |
| 6,413,496 | B1 | 7/2002 | Goodman et al. |
| 6,451,285 | B2 | 9/2002 | Blondino et al. |
| 6,461,591 | B1 | 10/2002 | Keller et al. |
| 6,645,466 | B1 | 11/2003 | Keller et al. |
| 6,713,047 | B1 | 3/2004 | Lewis et al. |
| 6,716,414 | B2 | 4/2004 | Lewis et al. |
| 6,987,094 | B2 * | 1/2006 | Malvolti et al. ............... 514/40 |
| 2001/0031244 | A1 | 10/2001 | Lewis et al. |
| 2003/0066525 | A1 | 4/2003 | Lewis et al. |
| 2003/0077230 | A1 | 4/2003 | Blondino et al. |
| 2003/0089369 | A1 | 5/2003 | Lewis et al. |

(Continued)

FOREIGN PATENT DOCUMENTS

| | | |
|---|---|---|
| EP | 0 372 777 | 6/1990 |
| EP | 0 504 112 A2 | 9/1992 |
| EP | 0 642 992 A2 | 3/1995 |
| EP | 0 653 204 | 5/1995 |
| EP | 0734 249 B1 | 10/1996 |
| EP | 0 911 048 | 4/1999 |
| EP | 1 157 689 | 11/2001 |
| GB | 1 525 181 | 9/1978 |
| GB | 2 326 334 | 12/1998 |
| WO | WO 91/11173 | 8/1991 |

(Continued)

OTHER PUBLICATIONS

Nikolaizik et al. (European Journal of Pediatrics, (Jul. 1996) vol. 155, No. 7, pp. 608-611).*

Nikolaizik et al, Eur. J. Pediatr, (1996) 155: pp. 608-611.

McCallion et al, International Journal of Pharmaceutics (1996) 130, pp. 1-11.

(Continued)

*Primary Examiner*—Shaojia Anna Jiang
*Assistant Examiner*—Michael C Henry
(74) *Attorney, Agent, or Firm*—Oblon, Spivak, McClelland, Maier & Neustadt, L.L.P.

(57) ABSTRACT

The invention provides a tobramycin formulation for delivery by aerosolization in the form of additive-free, isotonic solution whose pH has been optimised to ensure adequate shelf-life at room temperature. Said formulation can be advantageously used for the treatment and prophylaxis of acute and chronic endobronchial infections, in particular those caused by the bacterium *Pseudomonas aeruginosa* associated to lung diseases such as cystic fibrosis.

26 Claims, No Drawings

U.S. PATENT DOCUMENTS

| | | | |
|---|---|---|---|
| 2003/0157028 | A1 | 8/2003 | Lewis et al. |
| 2003/0190287 | A1 | 10/2003 | Lewis et al. |
| 2003/0190289 | A1 | 10/2003 | Lewis et al. |
| 2003/0206870 | A1 | 11/2003 | Lewis et al. |
| 2004/0047809 | A1 | 3/2004 | Lewis et al. |
| 2004/0062720 | A1 | 4/2004 | Lewis et al. |
| 2004/0096399 | A1 | 5/2004 | Lewis et al. |
| 2004/0184993 | A1 | 9/2004 | Lewis et al. |
| 2005/0129621 | A1 | 6/2005 | Davies et al. |
| 2005/0142071 | A1 | 6/2005 | Lewis et al. |
| 2005/0152846 | A1 | 7/2005 | Davies et al. |
| 2006/0083693 | A1 | 4/2006 | Lewis et al. |
| 2006/0120966 | A1 | 6/2006 | Church et al. |

FOREIGN PATENT DOCUMENTS

| | | |
|---|---|---|
| WO | WO 92/11236 | 7/1992 |
| WO | WO 92/20391 | 11/1992 |
| WO | WO 93/05765 | 4/1993 |
| WO | WO 93/11743 | 6/1993 |
| WO | WO 93/11747 | 6/1993 |
| WO | WO 93/18746 | 9/1993 |
| WO | WO 94/13262 | 6/1994 |
| WO | WO 94/14490 | 7/1994 |
| WO | WO 94/21228 | 9/1994 |
| WO | WO 94/21229 | 9/1994 |
| WO | WO 95/17195 | 6/1995 |
| WO | WO 96/12471 | 5/1996 |
| WO | WO 96/18384 | 6/1996 |
| WO | WO 96/19198 | 6/1996 |
| WO | WO 96/19968 | 7/1996 |
| WO | WO 96/19969 | 7/1996 |
| WO | WO 96/32099 | 10/1996 |
| WO | WO 96/32150 | 10/1996 |
| WO | WO 96/32151 | 10/1996 |
| WO | WO 96/32345 | 10/1996 |
| WO | WO 97/47286 | 12/1997 |
| WO | WO 98/01147 | 1/1998 |
| WO | WO 98/03533 | 1/1998 |
| WO | WO 98/05302 | 2/1998 |
| WO | WO 98/13031 | 4/1998 |
| WO | WO 98/24420 | 6/1998 |
| WO | WO 98/34595 | 8/1998 |
| WO | WO 98/34596 | 8/1998 |
| WO | WO 98/56349 | 12/1998 |
| WO | WO 99/12596 | 3/1999 |
| WO | WO 99/64014 | 12/1999 |
| WO | WO 99/65460 | 12/1999 |
| WO | WO 99/65464 | 12/1999 |
| WO | WO 00/06121 | 2/2000 |
| WO | WO 00/07567 | 2/2000 |
| WO | WO 00/23065 | 4/2000 |
| WO | WO 00/30608 | 6/2000 |
| WO | WO 00/35458 | 6/2000 |
| WO | WO 00/53157 | 9/2000 |
| WO | WO 00/78286 | 12/2000 |
| WO | WO 01/47493 | 7/2001 |
| WO | WO 01/89480 | 11/2001 |
| WO | WO 03/074023 | 9/2003 |

OTHER PUBLICATIONS

Mann et al, British Medical Journal, Aug. 25, 1984, vol. 289, p. 469.
Newman et al, Thorax, 1988, 43, pp. 318-322.
Smaldone et al, Journal of Aerosol Medicine, vol. 1, No. 2 (1988) pp. 113-126.
Thomas et al, Eur. Respir. J., (1991) vol. 4, pp. 616-622.
Wall et al, The Lancet, 1983, Jun. 11, 1983, p. 1325.
Ramsey et al, The New England Journal of Medicine, Jun. 17, 1993, vol. 328, No. 24, pp. 1740-1746.
The Lancet, Jul. 23, 1988, vol. II, p. 202.
Le Brun et al, International Journal of Pharmaceutics, Apr. 27, 1999, vol. 189, pp. 205-214.
Derbracher et al, Atemwegs und Lung, 1994, 20, pp. 381-382.
Machine translation of EP 0734249 Abstract Only.
Le Brun Pph et al., "Inhalation of tobramycin in cystic fibrosis Part 2: Optimization of the tobramycin solution for a jet and an ultrasonic nebulizer." International Journal of Pharmaceutics, vol. 189, No. 2, Nov. 5, 1999, pp. 215-225.
Brandl M and Gu L: "Degradation of tobramycin in aqueous solution," Drug Development and Industrial Pharmacy, vol. 18, No. 13, 1992, pp. 1423-1436.
R.O. Williams III et al, "A study of an epoxy aerosol can lining exposed to hydrofluoroalkane propellants" *European Journal of Pharmaceutics and Biopharmaceutics*, vol. 44, pp. 195-203, (1997).
*ABPI Compendium of Data Sheets and Summaries of Product Characteristics*. Datapharm Publications Limited, London, pp. 81-82, (1996-97).
Paul A. Sanders, Ph.D., "Homogeneous Systems and Their Properties", *Handbook of Aerosol Technology*, Second Edition, Van Nostrand Reinhold Company, NY, p. 30, 1979.
G. Brambilla et al, "Modulation of Aerosol Clouds Produced by HFA Solution Inhalers", *Portable Inhalers*, pp. 155-159, (Nov. 26 & 27, 1998).
B. Meakin, "Fine Particle Dose Control of Solution Based pMDIs", *Drug Delivery to the Lungs IX*, The Aerosol Society, pp. 1-20, (Dec. 14 & 15, 1998).
S.S. Davis, "Physico-Chemical Studies on Aerosol Solutions For Drug Delievery I. Water-Propylene Glycol Systems", *International Journal of Pharmaceutics*, 1, 1978, pp. 71-83.
L. Harrison et al, "Twenty-eight-day Double-blind Safety Study of an HFA-134a Inhalation Aerosol System in Healthy Subjects", *J. Pharm. Pharmacol.* 1996, vol. 48, pp. 596-600.
P. Hoet et al, "Epidemic of liver disease caused by hydrochlorofluorocarbons used as ozone-sparing substitutes of chlorofluorocarbons" *The Lancet*, 1997, vol. 350, pp. 556-559.
J. Daly, Jr., "Properties and toxicology of CFC alternatives", *Aerosol Age*, Feb. 1990, pp. 26-27, 40, 56 and 57.
D. Strobach, "Alternatives to CFCs" Part II, *Aerosol Age*, Jul. 1988, pp. 32-33, 42 and 43.
Tsi-Zong Tzou et al, "Drug Form Selection in Albuterol-Containing Metered-Dose Inhaler Formulations and Its Impact on Chemical and Physical Stability", *Journal of Pharmaceutical Sciences*, 1997, vol. 86, No. 12, pp. 1352-1357.
M.J. Kontny et al, "Issues Surrounding MDI Formulation Development with Non-CFC Propellants", *Journal of Aerosol Medicine*, 1991, vol. 4, No. 3, pp. 181-187.
I. P. Tansey, "Changing to CCF-Free Inhalers: The Technical and Clinical Challenges", *The Pharmaceutical Journal*, 1997, vol. 259, pp. 896-898.
D. Tiwari et al, Compatibility Evaluation of Metered-Dose Inhaler Valve Elastomers with Tetrafluoroethane (P134a), a Non-CFC Propellant, *Drug Development and Industrial Pharmacy*, 1998, vol. 24, No. 4, pp. 345-352.
*Handbook of Pharmaceutical Excipients*, 3rd Ed., Kibbe Editor, pp. 7-9, 220-222, 234-235 and 560-561.
L. I. Harrison et al, "Pharmacokinetics and Dose Proportionality of Beclomethasone From Three Strengths of a CFC-Free Beclomethasone Dipropionate Metered-Dose Inhaler", *Biopharmaceutics & Drug Disposition*, 1997, vol. 18, No. 7, pp. 635-643.
Chet Leach, "Enhanced Drug Delivery Through Reformulating MDIs with HFA Propellants-Drug Deposition and Its Effect on Preclinical and Clinical Programs", *Respiratory Drug Delivery V*, 1996, pp. 133-144.
G. Brambilla et al, "Modulation of Aerosol Clouds Produced By HFA Solution Inhalers", *Drug Delivery to the Lungs*, Dec. 14-15, 1998, The Aerosol Society.
Alexander Chuchalin et al., "A Formulation of Aerosolized Tobramycin (Bramitob®) in the Treatment of Patients with Cystic Fibrosis and *Pseudomonas aeruginosa* Infection," Padiatr. Drugs, 2007, vol, 9, pp. 21-31.

* cited by examiner

OPTIMISED FORMULATION OF TOBRAMYCIN FOR AEROSOLIZATION

CROSS REFERENCES TO RELATED APPLICATIONS

This application is a continuation of U.S. patent application Ser. No. 10/482,224, filed on Apr. 28, 2004, now U.S. Pat. No. 6,987,094, which is a 371 of International Patent Application No. PCT/EP02/06544, filed on Jun. 14, 2002, and claims priority to European Patent Application No. 01116071, filed on Jul. 2, 2001.

The present invention relates to tobramycin formulations for delivery by aerosolization.

SUMMARY OF THE INVENTION

The invention provides a tobramycin formulation for delivery by aerosolization in the form of additive-free, isotonic solution whose pH has been optimised to ensure adequate shelf-life at room temperature.

Said formulation can be advantageously used for the treatment and prophylaxis of acute and chronic endobronchial infections, in particular those caused by the bacterium *Pseudomonas aeruginosa* associated to lung diseases such as cystic fibrosis.

PRIOR ART

Although pressurised metered dose inhalers (MDIs) and dry powder inhalers (DPIs) are the most commonly used inhalation drug delivery systems, nebulisers have become increasingly popular for the treatment of airway obstruction, particularly in young children with asthma and in patients with severe asthma or chronic airflow obstruction. Nebulisers use ultrasound or compressed gas to produce aerosol droplets in the respirable size range (1- to 5 μm) from liquids, usually aqueous solutions or suspensions of drugs. They have the advantage over MDIs and DPIs that the drug may be inhaled during normal breathing through a mouth-piece or a face-mask. Thus, they can be employed to deliver aerosolised drug to patients, such as children, who experience difficulties using other devices.

Several types of therapeutically useful drug can be delivered by nebulisers, including β2-agonists, corticosteroids, anticholinergics, anti-allergics, mucolytics and antibiotics. The major clinical setting in which therapy with aerosolised antibiotics has been tried is the management of patients with cystic fibrosis (CF).

CF is a common genetic disease that is characterised by the inflammation and progressive destruction of lung tissue. The debilitation of the lungs in CF patients is associated with accumulation of purulent sputum produced as a result of endobronchial infections caused in particular by *Pseudomonas aeruginosa*. The latter ones are a major cause of morbidity and mortality among patients with CF.

Tobramycin is an aminoglycoside antibiotic specifically active against *Pseudomonas aeruginosa*. It penetrates endobronchial secretions (sputum) poorly, necessitating large intravenous doses to attain an efficacious concentration at the site of infection. These high doses place the patient at risk for nephrotoxic and ototoxic effects. The direct delivery of tobramycin to the lower airways by aerosol administration is attractive, since it produces high concentrations of antibiotic at the site of infection. In view of the limited absorption into the circulation, aerosol delivery of tobramycin should be associated with minimal systemic toxicity. This would allow for the development of a safer, long-term therapy.

At this regard, being its therapeutic dose quite large, nebulisation turns out to be extremely convenient due to the impossibility of formulating tobramycin into an MDI or DPI.

The clinical studies reported in the literature show contradictory results in terms of benefit from aerosolised tobramycin in patients with CF. The variability among these studies might, in part, result from the differences in the patient population, therapeutic modalities, nebulisers, formulations and their mode of administration. Furthermore, most of the studies have been carried out through the extemporaneous use of the commercially available injectable solutions. These preparations normally contain anti-oxidant and preservatives which are known to cause paradoxical reactions such as bronchospasm and cough (Nikolaizik et al Eur J Pediatr 1996, 155, 608-611; The Lancet, Jul. 23 1988, 202).

For all these reasons, there is a need for standardised procedures as well as for improvement in aerosol administration of antibiotic such as tobramycin to CF patients.

Therefore, in consideration of all problems outlined, it would be highly advantageous to provide a tobramycin formulation of a therapeutically useful concentration deliverable by aerosolization into the endobronchial space which: i) could be efficiently nebulised in a relatively short time using both jet and ultrasonic nebulisers; ii) could permit generation of aerosol well-tolerated by patients; iii) is able to produce aerosol particles which can efficaciously reach the therapeutic target area; iv) is rid of substances (preservatives and others) that may give rise to undesirable side effects; v) could guarantee as long as possible a shelf-life, in particular at room temperature.

Accordingly, in order to obtain an optimised formulation for tobramycin aerosol administration, the following parameters need to be carefully adjusted:

- The ratio dose/volume. Formulation for aerosol delivery should contain the minimal yet efficacious amount of tobramycin formulated in the smallest as possible volume of solution. In fact, the smallest the volume, the shortest the nebulisation time. A short nebulisation time, in turn, is an important determinant of patient compliance and within hospitals has implications for staff time (McCallion et al Int J Pharm 1996, 130, 1-11).
- The osmolarity. It is well known that adverse reactions to inhalation therapy may be caused by hypo- or hyper-osmolarity of drug solutions. On the contrary, isotonic solutions remove the risk of paradoxical bronchoconstriction and cough (The Lancet, 1988, op. cit.; Mann et al Br Med J 1984, 289, 469). The osmolarity also affects the performances of the nebulisers in terms of output rate and particle size distribution (vide ultra).
- The particle size distribution upon nebulisation. The efficacy of a clinical aerosol is dependent on its ability, to penetrate the respiratory tract. To penetrate to the peripheral regions, aerosols require a size from 0.8 to 5 μm, with a size of about 3 μm preferable for alveolar deposition. Particles smaller than 0.5 μm are mainly exhaled. Besides the therapeutic purposes, the size of aerosol particles is important in respect to the side effects of the drugs. Larger droplets deposited in the upper respiratory tract are indeed rapidly cleared from the tracheo-bronchial tract by the mucociliary clearance process, with the effect that drug becomes available for systemic absorption and potentially adverse effects. Several authors (Newman et al Thorax 1988, 43, 318-322; Smaldone et al J Aerosol med, 1988, 1, 113-126; Thomas et al. Eur Respir J 1991, 4, 616-622) have suggested that close attention to the droplet size of the aerosolised drug for the antibiotic treatment of CF must be paid, since penetration to the peripheral airways is particularly desirable.

The pH of the formulation. An important requirement for an acceptable formulation is its adequate shelf-life suitable for commercial, distribution, storage and use. Generally, tobramycin intravenous solutions contain phenol or other preservatives and anti-oxidants to maintain potency and to minimise the formation of degradation products that may colour the solution. However, as already pointed out, said substances may induce unwanted reactions in patients with lung diseases such as CF. The stability of tobramycin strictly depends on the pH. Therefore, the pH of its formulations need to be carefully adjusted in order to slow or prevent degradation products formation without the aid of preservatives and/or anti-oxidants; it would also be advantageous to adjust pH in such a way as to prevent as much as possible discoloration although the depth of colour is not a reliable indicator of the extent of oxidation. Formulations provided of adequate shelf-life under environmental storage conditions (room temperature and, at the occurrence, protected form light) would be particularly preferred, since the stability at room temperature of the preparations of the prior art are rather unsatisfactory. During use, the formulation prepared according to EP 734249 marketed under the trade-name of Tobi® could be indeed kept at room temperature for only 28 days.

OBJECT OF THE INVENTION

It is an object of the invention to provide a formulation to be administered by nebulisation suitable for well-tolerated and efficacious delivery of tobramycin into the endobronchial space for treating *Pseudomonas aeruginosa* and/or other susceptible bacterial infections associated to pulmonary diseases such as CF.

In particular, it is an object of the invention to provide a formulation in the form of aqueous solution to be administered by nebulisation, wherein tobramycin concentration, tonicity and pH have been optimised for guaranteeing better compliance of the patients, maximal tolerance and efficacy and as long as possible a shelf-life at room temperature.

According to the present invention there is provided a formulation constituted of 7.5% w/v tobramycin in 0.45% w/v sodium chloride aqueous solution having a pH of between 4.0. and 5.5 and osmolarity between 250 and 450 mOsm/l (approximately equivalent to mOsm/kg).

In a preferred embodiment of the invention, the formulation contains 300 mg of tobramycin sulfate in 4 ml of half-saline aqueous solution (0.45% of sodium chloride) in order to have an osmolarity ranging from 280 to 350 mOsm/l and it has a pH of 5.2.

In the prior art, several tobramycin formulations for inhalation have been proposed for the treatment of patients with CF and *Pseudomonas aeruginosa* infections.

Most of the commercially available tobramycin solution for injection when extemporarily used for inhalation can cause significant bronchial obstruction as they are not preservative-free but contain anti-oxidants such as sodium EDTA and/or, sodium metabisulphite and preservatives such as phenol.

Wall et al (The Lancet, 1983, Jun. 11, 1325) reported the result of a clinical study upon inhalation of 80 mg tobramycin plus 1 g ticarcillin twice daily from a hand-held nebuliser. On their own admission, one of the drawbacks of the regimen is the time required for inhalation (about 30 min).

Ramsey et al (New Eng J Med 1993, 328, 1740-1746) conducted an extensive study to evaluate the safety and efficacy of aerosolised tobramycin. For reaching the target concentration (≧400 μg per gram of sputum), they used 600 mg of preservative-free tobramycin sulfate dissolved in 30 ml of half-strength physiologic saline, adjusted to a pH of 6.85 to 7.05. The large volume was required by the ultrasonic nebuliser used (DeVilbiss). Besides the long term required for inhalation, the pH is not optimal either. From a stability point of view, it is known that, at pH around neutrality, tobramycin rapidly oxidises although it is very stable towards hydrolysis (Brandl et al Drug Dev Ind Pharm 1992, 18, 1423-1436). Common Compendia (Martindale, Physician Desk Reference) suggest indeed to maintain tobramycin solution at a pH comprised between 3.0 and 6.5.

EP 734249 claims a formulation comprising from 200 mg to 400 mg of aminoglycoside dissolved in about 5 ml of solution containing 0.225% of sodium chloride (1/4 normal saline -NS-) and having pH between 5.5 and 6.5. According to the inventors, the formulation contains minimal yet efficacious amount of aminoglycoside formulated in a small as possible a volume of physiologically acceptable solution having a salinity adjusted to permit generation of aminoglycoside aerosol well-tolerated by patients but preventing the development of secondary undesirable effects, such as bronchospasm and cough (pg. 4, lines 51-55). The preferred tobramycin formulation containing 1/4 NS with 60 mg of tobramycin per ml of 1/4 NS (which equates to 6% w/v) has a pH of about 6.0 and an osmolarity in the range of 165-190 mOsm/l. According to the inventors, the osmolarity range is within the safe range of aerosols administered to a cystic fibrosis patient and a further advantage of the quarter normal saline, i.e. saline containing 0.225% of sodium chloride with 60 mg/ml tobramycin is that this formulation is more efficiently nebulised by an ultrasonic nebuliser compared to tobramycin formulated in a solution 0.9% normal saline (pg. 5, lines 50-54). The inventors state that a more concentrated solution (in comparison to 60 mg per ml) will increase the osmolarity of the solution, thus decreasing the output of the formulation with both jet and ultrasonic nebulisers. Alternatively, a more concentrated solution in a smaller volume is also disadvantageous due to the typical dead space volume of the nebulisers (1 ml): that means that the last 1 ml of solution is wasted because the nebuliser is not fully performing (pg. 6, lines 35-38). The claimed pH range was found to be optimal from the storage and longer shelf-life point of view (page 7 lines 2-3) but, indeed, it allows to achieve completely stable solutions at 5° C. and effectively stable ones at room temperature for 6 months; moreover the claimed formulation remains within an acceptable range of color obtained upon storage in pouch (so protected from light), but there is no data referring to its behavior outside the pouch.

A pH between 5.5 and 6.5 was claimed because, in the Opinion of the inventors, any aerosol with a pH of less than 4.5 usually will induce bronchospasm in a susceptible individual and aerosols with a pH between 4.5 and 5.5 will occasionally cause this problem (pg. 5, line 58-pg. 6, line 1) Le Brun et al Int J Pharm 1999, 189, 205-214 disclosed a 10% w/v tobramycin solution for inhalation having a pH of 7.5. The same authors (Int J Pharm 1999, 189, 215-225), in a further study aiming at developing highly concentrated solutions, have studied the aerosolization properties of several tobramycin solutions, ranging from 5 to 30% w/v. All the solutions disclosed in this paper have a pH around the neutrality and exhibit an osmolarity far away from an isotonic value (282 mOsm/l).

In none of aforementioned documents the features of the formulation of the present invention are disclosed and none of the teaching therein disclosed fully contributes to the solution of the problem underlying the invention, to provide a concentrated solution to be delivered by aerosol in a smaller volume, with a tonicity closer to the physiological value.

The use of a more concentrated solution with respect to that reported as optimal in the prior art (7.5% vs. 6.0% w/v) allows to employ vials with a smaller volume, so allowing, in turn, to reduce the time of nebulisation. Although it is true that some nebulisers have a dead space volume of 1 ml, other have a minor one (0.5 ml or less), so the wasting of using vials of 4 ml would be only approx. 10% or less.

According to the invention, the osmolarity of the formulation is within the range of solutions considered as isotonic, whereas both the formulations of EP 734249 and Ramsey et al have an osmolarity, i.e. 165-190 mOsm/l, typical of solutions considered as hypotonic (Derbracher et al Atemwegs und Lung 1994, 20, 381-382). Although the formulations of the prior art turned out to be safe, only isotonic solutions may completely prevent the risk of paradoxical bronchoconstriction. Moreover, the results reported in the example 2 indicate that the formulations having an osmolarity in the range claimed, contrary to what stated in EP 734249, are efficiently nebulised despite their higher concentration.

The pH between 4.0 and 5.5, preferably 5.2, was found to be optimal in terms of storage and shelf-life at room temperature. Long-term stability studies show that tobramycin in the formulation of the present invention is stable for over nine months. Moreover, for all that period, its colour does not significantly change and remains within an acceptable range even if not stored in a foil overpouch.

According to a further embodiment of the invention, there is also provided a process for the preparation of such formulation, said process including the steps of:

i) preparing an aqueous solution containing 0.45% w/v of sodium chloride;
ii) adjusting the pH with a concentrated strong acid;
iii) adding the active ingredient and mixing to complete dissolution;
iv) re-adjusting the pH to the desired value;
v) filling the solution in suitable containers, preferably pre-sterilised by filtration.

The aerosol formulations of the invention refer to a 7.5% w/v aqueous solution of an antibiotic of the aminoglycoside family, preferably tobramycin and salts thereof, for the treatment of lung infections due to Gram positive and negative bacteria, in pulmonary diseases such as cystic fibrosis, non-CF bronchiectasis infected with *Pseudomonas aeruginosa* and other chronic pneumopathies, particularly in an exacerbation phase, such as bronchiectasis, COPD and bronchial asthma.

The osmolarity of the formulation should range between 250 and 450 mOsm/l, preferably between 260 and 400, even more preferably between 280 and 350 mOsm/l; it can be adjusted by using any physiologically acceptable salt or non-volatile compounds; preferably, tobramycin is dissolved in a 0.45% w/v sodium chloride aqueous solution.

The pH can be adjusted by using any concentrated strong acid, preferably sulfuric acid and should range from 4.0 to 5.5, preferably from 5.0 to 5.4.

The formulations of the invention can be distributed in suitable containers such as multidose vials or pre-sterilised unit dose vials of 2 or 4 ml, depending on the therapeutic indication; otherwise, the vials can be aseptically filled using the "blow, fill and seal" technology. The filling is preferably carried out under inert atmosphere. The solution formulations can be advantageously sterilised by filtration.

The invention is illustrated by the following examples.

EXAMPLE 1

Preparation of the 7.5% w/v Tobramycin Solution at pH 5.2 and Stability Studies The composition refers to 1 unit-dose vial (2 ml)

| Ingredient | Quantity |
|---|---|
| Tobramycin | 150 mg |
| Sodium chloride | 9 mg |
| Sulphuric Acid 2N | q.s. to pH 5.2 ± 0.2 |
| Sodium hydroxide 1M* | q.s to pH 5.2 ± 0.2 |
| Purified water | q.s. to 2 ml |

*added only if required.

Sodium chloride is dissolved into 40 l of purified water (mix for 15 minutes to guarantee the NaCl complete dissolution). Then, 30 l of sulphuric acid (2N $H_2SO_4$) is added to the saline solution; during the operation, the solution temperature is monitored. When the solution temperature is about 25÷30° C., $N_2$ is insufflated to obtain a value of dissolved $O_2$ less than 1 mg/l. Afterwards, tobramycin is added and mixed to complete dissolution (for not less than 15 minutes) while the temperature is maintained below 25-30° C. The pH value is checked and, if necessary, sulphuric acid 2N or sodium hydroxide solution 1M are added to obtain a pH value of 5.2±0.2. When the solution temperature is 25° C.±2° C., purified water is added to reach the final volume. The resulting solution is mixed for 15 minutes. The pH value is checked again and, if necessary, sulphuric acid 2N or sodium hydroxide solution 1M are added to obtain a pH value of 5.2±0.2. The solution is, filtered through one 0.45 μm Nylon filter, and through two 0.2 μm Nylon filters.

The solution is distributed in 2 ml polyethylene colorless unit dose vials under nitrogen purging.

The stability of the vials was evaluated both under long-term (25° C., 60% R.H.) and accelerated conditions (40° C., 75% R.H.) [R.H.=relative humidity]. Results are reported in Tables 1 and 2, respectively. Assays of tobramycin and of its main related substances (degradation products) were determined by HPLC. Residual oxygen, pH and osmolarity were also assayed. The osmolarity was measured using a freezing-point depression osmometer.

The formulation of the invention turns out to be stable for at least 9 months at room temperature and for 6 months under accelerated conditions. pH and osmolarity remain substantially unchanged under both conditions. At room temperature, the colour of the formulation of the invention does not significantly change and remains within an acceptable range even if not stored in a foil overpouch.

TABLE 1

Stability under long-term conditions (25° C., 60% R.H.)

| | TECHNOLOGICAL CONTROLS | | | CHEMICAL CONTROLS | | |
|---|---|---|---|---|---|---|
| Analysis | Solution appearance | Oxygen mg/l | Osmolarity mOsm/l | Tobramyicin mg/ml (%) | pH | Related substances % |
| Specification range | Clear pale yellow solution | (a) | 260-350 | 67.5-82.5 | 4.5-5.5 | (a) |
| t = 0 | Clear pale yellow solution | 2.8 | 321 | 75.8 (100) | 5.2 | 6.39 |
| t = 3 months | Clear pale yellow solution | 2.9 | 314 | 76.6 (101.1) | 5.2 | 6.35 |
| t = 6 months | Clear pale yellow solution | 3.0 | 304 | 75.4 (99.5) | 5.0 | 5.84 |
| t = 9 months | Clear pale yellow solution | 2.8 | 293 | 76.5 (100.9) | 5.1 | 6.27 |

(a) not established

TABLE 2

Solution of example 1 - Stability under accelerated conditions (40° C., 75% R.H.)

| | TECHNOLOGICAL CONTROLS | | | CHEMICAL CONTROLS | | |
|---|---|---|---|---|---|---|
| Analysis | Solution appearance | Oxygen mg/l | Osmolarity mOsm/l | Tobramycin mg/ml (%) | pH | Related substances % |
| Specification range | Clear pale yellow solution | (a) | 260-350 | 67.5-82.5 | 4.5-5.5 | (a) |
| t = 0 | Clear pale yellow solution | 2.8 | 321 | 75.8 (100) | 5.2 | 6.39 |
| t = 1 months | Clear pale yellow solution | 2.7 | n.d. | 78.3 (103.3) | 5.1 | 6.42 |
| t = 3 months | Clear yellow solution | 2.8 | 311 | 75.3 (99.3) | 5.1 | 5.48 |
| t = 6 months | Clear yellow solution | 3.2 | 292 | 77.1 (101.7) | 4.7 | 6.17 |

(a) not established;
(n.d.) not determined

EXAMPLE 2

The nebulisation efficiency of the solution for inhalation of example 1, expressed as percentage of active ingredient nebulised, was evaluated using a commercial jet nebuliser (PARI-BOY) for a 5-minute nebulisation time. The size profile of the droplets produced by nebulisation of the solution, expressed as diameter (μm) below which respectively 10%, 50% and 90% of the droplets are included, was also characterised by Malvern analysis.

A formulation prepared according to the teaching of the preferred embodiment of EP 734249, i.e. containing 60 mg of active ingredient per ml of 0.225% sodium chloride aqueous solution and having a pH of about 6, was nebulised for comparison. Both formulations were filled in 2 ml unit dose vials. The results are reported in Table 3 as a mean of two determinations.

TABLE 3

| | Osmolarity | Malvern Analysis (μm) | | | Efficiency |
|---|---|---|---|---|---|
| | (mOsm/l) | 10% | 50% | 90% | (%) |
| Formulation of ex. 1 | 295 | 1.61 | 6.26 | 13.46 | 47.4 |
| Formulation of EP 734249 | 222 | 1.78 | 6.24 | 13.46 | 42.2 |

The results indicate that the formulation according to example 1 having an osmolarity near isotonicity is efficiently nebulised.

The size profile of the droplets produced by nebulisation is instead practically the same.

The invention claimed is:

1. An aerosol formulation, comprising:

75 mg/ml of tobramycin dissolved in an aqueous solution containing 0.45% w/v of sodium chloride;

wherein the pH is between 4.5 and 5.5 and the osmolarity ranges between 250 and 450 mOsm/l, and said formulation is free of preservatives and anti-oxidants.

2. The aerosol formulation according to claim 1, wherein the pH is 5.2 and the osmolarity is between 280 and 350 mOsm/l.

3. A process for the preparation of an aerosol formulation according to claim 1, comprising:

i) preparing an aqueous solution containing 0.45% w/v of sodium chloride;

ii) adjusting the pH with a concentrated strong acid;

iii) adding the active ingredient and mixing to complete dissolution;

iv) re-adjusting the pH to the desired value;

v) filling a suitable container with the solution.

4. The process according to claim 3, wherein the solution is pre-sterilized by filtration.

5. The aerosol formulation according to claim 1, wherein said osmolarity is 280 to 350 mOsm/l.

6. The process according to claim 3, wherein the concentrated strong acid is sulfuric acid.

7. The process according to claim 3, wherein in step ii) the pH is adjusted to 4.0 to 5.5.

8. The process according to claim 3, wherein in step iv) the pH is re-adjusted to 4.0 to 5.5.

9. The process according to claim 3, wherein said container is a multidose vial.

10. The process according to claim 3, wherein said container is a pre-sterilized unit vial of 2 ml.

11. The process according to claim 3, wherein said container is a pre-sterilized unit vial of 4 ml.

12. The process according to claim 3, wherein said filling in step v) is carried out under an inert atmosphere.

13. The aerosol formulation according to claim 1, which is stable for at least 9 months at room temperature.

14. An aerosol formulation, comprising 75 mg/ml of tobramycin dissolved in an aqueous solution containing 0.45% w/v of sodium chloride, wherein:

the formulation has a pH of from 4.0 to 5.5;

the formulation has an osmolarity of from 250 to 450 mOsm/l.

15. The aerosol formulation according to claim 1, wherein said osmolarity is 292 to 350 mOsm/l.

16. The aerosol formulation according to claim 1, wherein said osmolarity is 293 to 350 mOsm/l.

17. The aerosol formulation according to claim 1, wherein said osmolarity is 295 to 350 mOsm/l.

18. The aerosol formulation according to claim 1, wherein said osmolarity is 304 to 350 mOsm/l.

19. The aerosol formulation according to claim 1, wherein said osmolarity is 311 to 350 mOsm/l.

20. The aerosol formulation according to claim 1, wherein said osmolarity is 314 to 350 mOsm/l.

21. The aerosol formulation according to claim 14, wherein said osmolarity is 292 to 350 mOsm/l.

22. The aerosol formulation according to claim 14, wherein said osmolarity is 293 to 350 mOsm/l.

23. The aerosol formulation according to claim 14, wherein said osmolarity is 295 to 350 mOsm/l.

24. The aerosol formulation according to claim 14, wherein said osmolarity is 304 to 350 mOsm/l.

25. The aerosol formulation according to claim 14, wherein said osmolarity is 311 to 350 mOsm/l.

26. The aerosol formulation according to claim 14, wherein said osmolarity is 314 to 350 mOsm/l.

* * * * *